(12) United States Patent
Miura et al.

(10) Patent No.: US 8,159,656 B2
(45) Date of Patent: *Apr. 17, 2012

(54) METHOD AND APPARATUS FOR EVALUATING ULTRAVIOLET RADIATION PROTECTION EFFECT

(75) Inventors: Yoshimasa Miura, Yokohama (JP);
Masayuki Shirao, Yokohama (JP);
Takashi Ohmori, Yokohama (JP);
Takuya Saiwaki, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 330 days.

This patent is subject to a terminal disclaimer.

(21) Appl. No.: 12/443,849

(22) PCT Filed: Oct. 4, 2007

(86) PCT No.: PCT/JP2007/069474
§ 371 (c)(1),
(2), (4) Date: Apr. 1, 2009

(87) PCT Pub. No.: WO2008/044596
PCT Pub. Date: Apr. 17, 2008

(65) Prior Publication Data
US 2010/0014069 A1  Jan. 21, 2010

(30) Foreign Application Priority Data
Oct. 6, 2006  (JP) .................... 2006-274783

(51) Int. Cl.
*G01J 3/00* (2006.01)
(52) U.S. Cl. .......... 356/51; 356/306; 356/326; 250/372

(58) Field of Classification Search .................... 356/51, 356/306, 326; 250/372; 702/19, 30, 32
See application file for complete search history.

(56) References Cited

U.S. PATENT DOCUMENTS

| 4,749,865 | A | * | 6/1988 | Scheller ..................... 250/338.1 |
| 5,500,533 | A | * | 3/1996 | Ogawa et al. ................. 250/372 |
| 5,640,957 | A | * | 6/1997 | Kaminski et al. ............. 600/407 |
| 7,567,080 | B2 | * | 7/2009 | Ferrero et al. ................ 324/309 |

(Continued)

FOREIGN PATENT DOCUMENTS
EP       1291640       3/2003
(Continued)

OTHER PUBLICATIONS

A New Substrate to measure sunscreen protection factors throughout the ultraviolet spectrum; Journal of the Society of Cosmetic Chemists (1989) 40:33, 127-133.

(Continued)

*Primary Examiner* — Tarifur Chowdhury
*Assistant Examiner* — Michael P Lapage
(74) *Attorney, Agent, or Firm* — IPUSA, PLLC (57) ABSTRACT

A first step of measuring a change over time in the spectral transmission spectrum of a measurement sample by its exposure to the light of a light source including an ultraviolet radiation for a preset light exposure time, a second step of performing a correction according to the change over time in the spectral transmission spectrum of the measurement sample based on the result of the measurement obtained by the first step, and a third step of calculating the final in vitro predicted SPF of the measurement sample using the result of the correction obtained by the second step are included.

8 Claims, 4 Drawing Sheets

U.S. PATENT DOCUMENTS

2004/0195519 A1 10/2004 Refregier et al.
2005/0236576 A1* 10/2005 Yagi .............................. 250/372
2008/0224059 A1* 9/2008 Ferrero et al. ................ 250/372

FOREIGN PATENT DOCUMENTS

| FR | 2710151 | 3/1995 |
|---|---|---|
| JP | 07-167781 | 7/1995 |
| JP | 2005-034350 | 2/2005 |

OTHER PUBLICATIONS

A Reference Action Spectrum for Ultraviolet Induced Erythema in Human Skin; CIE Journal (1987)6:1, 17-22.

International Sun Protection Factor (SPF) Test Method, Feb. 2003.

Photodegradation of Sunscreen Chemicals: Solvent Considerations, Cosmetics & Toiletries [1999] 105: 41-44.

Extended European Search Report mailed Nov. 28, 2011.

Stokes R et al: "In vitro assessment of sunscreen photostability: the effect of radiation source, sunscreen application thickness and substrate", International Journal of Cosmetic Science, Kluwer Academic Publishers, Dordrecht, NL, vol. 21, Jan. 1, 1999, pp. 341-351, XP002263133.

Stanfield J: "Sunscreen photostability and UVA protection", Journal of Cosmetic Science, Society of Cosmetic Chemists, New York, NY, US, vol, 52, Jan. 1, 2001, pp. 412-413, XP008129660.

Stanfield J: "Optimizing in vitro measurement of sunscreen protection", SOFW-Journal Seifen, Oele, Fette, Wachse, Verlag Fur Chemische Industrie, Augsburg, DE, vol. 132, No. 7, Jul. 1, 2006, pp. 19-23, XP008129662.

* cited by examiner

(a) PRELIMINARY MEASUREMENT (b) FINAL MEASUREMENT

METHOD AND APPARATUS FOR EVALUATING ULTRAVIOLET RADIATION PROTECTION EFFECT

TECHNICAL FIELD

The present invention relates to a method and apparatus for measuring an ultraviolet radiation protection effect.

BACKGROUND ART

The SPF (Sun Protection Factor) is used as a scale representing the ultraviolet radiation protection effect of cosmetic products for preventing sunburn due to ultraviolet radiation (so-called sun protection products). This SPF, which is an index indicating the effect of skin protection from sunburn due to ultraviolet radiation and sunburn preventions is defined by the value obtained by dividing the amount of ultraviolet radiation necessary for causing slight redness in the case of using a sun protection product by the amount of ultraviolet radiation necessary for causing slight redness in the case of not using a sun protection product. This means that with, for example, a sun protection product of SPF 10, the same sunburn (erythema) as that on bare skin is caused by exposure to ten times as much ultraviolet radiation as in the case of causing sunburn on bare skin. In measuring the SPF, artificial light (a solar simulator) very close to sunlight is adopted in place of sunlight that may vary in value depending on the season or location. The measurement is performed by exposing each of unprotected skin and protected skin to a certain amount of ultraviolet radiation and determining the next day whether erythema has been caused.

Using the SPF measured based on the above-described method makes it possible to objectively evaluate the ultraviolet radiation protection effect of sun protection products. However, the above-described method necessitates the cooperation of a large number of volunteers of specific skin types, thus requiring a large amount of money and a large number of days. Accordingly, it has been desired to develop an in vitro and simple method of calculating in vitro predicted SPFs having high correlation with the in vivo SPFs obtained by the above-described method for, for example, evaluation of the ultraviolet radiation protection effect of a product under development.

Conventionally known methods of evaluating an ultraviolet radiation protection effect by in vitro measurement includes a dilution method that measures the ultraviolet radiation absorbance or transmittance of a sample diluted with an organic solvent in a quartz cell and a thin film method that measures the ultraviolet radiation absorbance or transmittance of a sample formed into a film having even thickness on a quartz plate. These conventional methods are significant in understanding characteristics such as the absorption maximum wavelength and protection wavelength region of an ultraviolet absorber, but cannot predict the SPF. This is because these methods for evaluating an ultraviolet radiation protection effect differ greatly from methods for measuring in vivo SPFs. Further, the biological reaction represented by the SF depends on the ultraviolet wavelength, and the erythema reaction is likely to occur at some ultraviolet wavelengths and is less likely to occur at other ultraviolet wavelengths. Therefore, it has been considered necessary to take the effect on a living body into consideration on a wavelength basis.

With respect to the above-described two problems, Non-Patent Document 1 applies a sample on a medical tape serving as a skin substitute film and measures the spectral transmission spectrum of the sample. This measurement result is subjected to calculation by the Diffey & Robson formula to calculate the SPF. This Diffey & Robson formula succeeds in solving the above-described problems by countering the wavelength dependence of the erythema reaction as a human biological reaction by using an erythema factor disclosed in Patent Document 2.

However, in vivo SPFs include various factors such as an individual difference, a regional difference, an age difference, a gender difference, and a skin type difference. Therefore, it has been considered a problem that it is actually very difficult to predict the SPF with accuracy based only on the single example of the erythema factor.

Therefore, an evaluation method has been proposed that can predict the in vitro SPFs of even unknown samples not by adopting only the erythema factor but by deriving an arithmetic expression capable of obtaining statistically high correlation from the relationship between a large number of samples with known in vivo SPFs and their spectral transmission spectra. (See, for example, Patent Document 1.) This evaluation method makes it possible to obtain in vitro predicted SPFs with accuracy and has eliminated variation factors arising from an individual difference, a regional difference, an age difference, a gender difference, a skin type difference, etc.

[Non-Patent Document 1] Journal of the Society of Cosmetic Chemists (1989) 40:33, 127-133
[Non-Patent Document 2] CIE Journal (1987) 6:1, 17-22
[Patent Document 1] U.S. Pat. No. 3,337,832

DISCLOSURE OF THE INVENTION

Problem(s) To Be Solved By The Invention

However, the method of evaluating an ultraviolet radiation protection effect disclosed in Patent Document 1 described above has a problem in that it is possible to make accurate predictions up to approximately SPF 30 but it is not possible to make accurate predictions with respect to samples of SPF 30 or higher SPFs. In recent years, mainstream products have SPF 50 or higher SPFs, and products having yet higher SPFs are expected to be launched in the future.

Further, there have been many findings on the photodegradation phenomenon of an ultraviolet absorber due to ultraviolet light lately. Therefore, reproducing the same light exposure conditions as the conditions for measuring in vivo SPFs and thereby correctly estimating a corresponding decrease in the SPF are considered necessary for accurate prediction of the SPF in the method of calculating in vitro SPF predicted values as well.

The present invention is made in view of the above-described points, and has an object of providing a method of evaluating an ultraviolet radiation protection effect based on in vitro measurement, which method reflects the photodegradation phenomenon of a sample due to exposure light and shows a high correlation with in vivo SPFs even in samples with high SPFs, and an apparatus for evaluating an ultraviolet radiation protection effect using this method.

Means for Solving the Problem(s)

The present invention is characterized by taking the following measures in order to achieve the above-described object.

A method of evaluating an ultraviolet radiation protection effect according to the present invention includes a first step of measuring a change over time in a spectral transmission spectrum of a measurement sample by an exposure thereof to a light of a light source including an ultraviolet radiation for a preset light exposure time, a second step of performing a correction according to the change over time in the spectral transmission spectrum of the measurement sample based on a result of the measurement obtained by the first step, and a third step of calculating a final in vitro predicted SPF of the measurement sample using a result of the correction obtained by the second step.

Further, an apparatus for evaluating an ultraviolet radiation protection effect according to the present invention includes temporal change measurement means for measuring a change over time in a spectral transmission spectrum of a measurement sample by an exposure thereof to a light of a light source including an ultraviolet radiation for a preset light exposure time, correction means for performing a correction according to the change over time in the spectral transmission spectrum of the measurement sample based on a result of the measurement obtained by the measurement means, and predicted SPF calculation means for calculating a final in vitro predicted SPF of the measurement sample using a result of the correction obtained by the correction means.

Effects of the Invention

According to the present invention, it is possible to provide a method of evaluating an ultraviolet radiation protection effect based on in vitro measurement, which method reflects the photodegradation phenomenon of a sample due to exposure light and shows high correlation with in vivo SPFs even in samples with high SPFs, and an apparatus for evaluating an ultraviolet radiation protection effect using this method.

| DESCRIPTION OF THE REFERENCE NUMERALS | |
|---|---|
| 10 | Ultraviolet radiation protection effect evaluation apparatus |
| 11 | Light source |
| 12 | Filter |
| 13 | Optical fiber |
| 14 | irradiation port |
| 15 | Sample |
| 16 | Skin substitute film |
| 17 | Spectrometer |
| 18 | Photodetector |
| 19 | Computer |
| 21 | Input means |
| 22 | Output means |
| 23 | Storage means |
| 24 | Spectral transmission spectrum measurement means |
| 25 | Light exposure time determination means |
| 26 | Temporal change measurement means |
| 27 | Correction means |
| 28 | Predicted SPF calculation means |
| 29 | Control means |

BEST MODE(S) FOR CARRYING OUT THE INVENTION

Next, a description is given, with reference to the drawings, of the best mode(s) for carrying out the invention.

A method of evaluating an ultraviolet radiation protection effect and an apparatus for evaluating an ultraviolet radiation protection effect using this method according to this embodiment performs, for example, a final measurement made up of a first step of measuring a change over time in the spectral transmission spectrum of a measurement sample by its exposure to the light of a light source including ultraviolet radiation for a preset light exposure time, a second step of performing correction according to the obtained change over time in the spectral transmission spectrum, and a third step of calculating the final in vitro predicted SPF of the measurement sample.

In the first step, for example, a preliminary measurement may be performed that is made up of a step of measuring the spectral transmission spectrum of the measurement sample at intervals of 1 nm with 290 nm to 400 nm ultraviolet radiation and a step of determining the light exposure time in a final measurement described below from the obtained spectral transmission spectrum. A description is given below of this method and apparatus.

[Schematic Configuration of Evaluation Apparatus]

Figure 1:
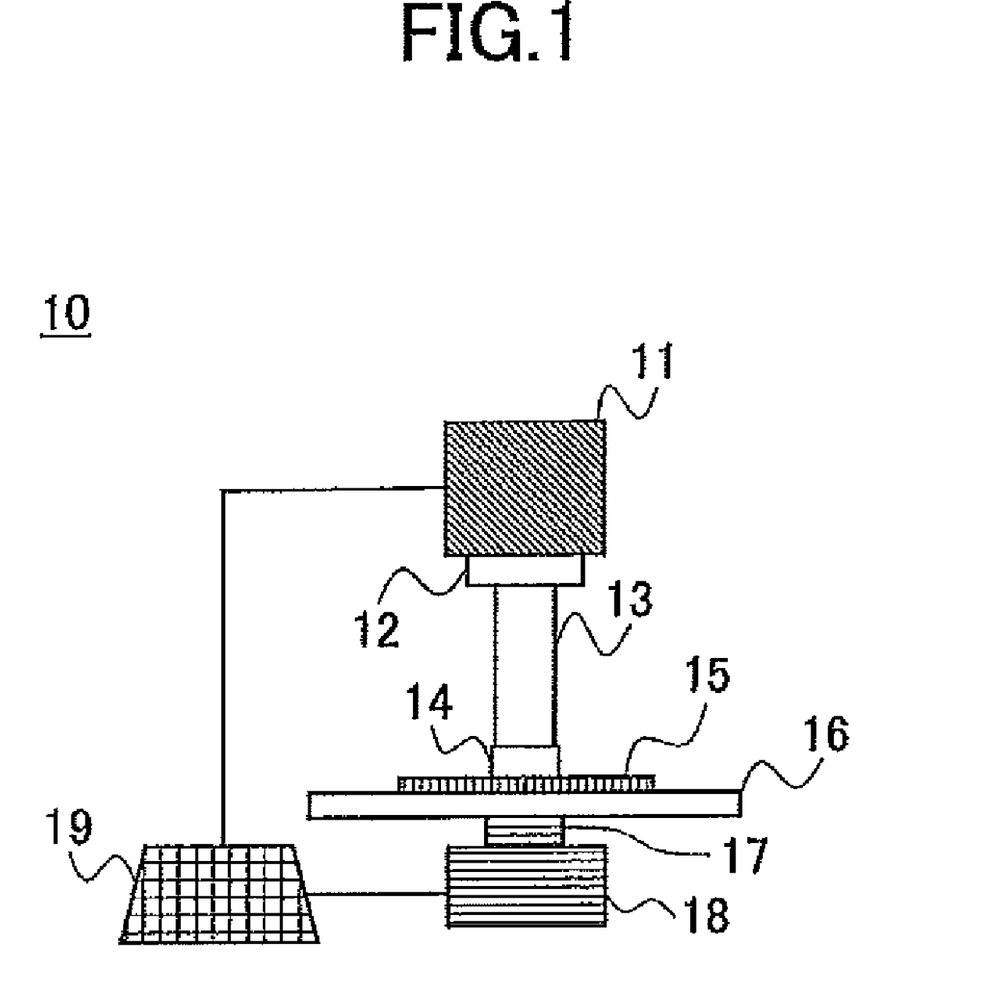
FIG. 1 is a diagram illustrating a schematic configuration of an apparatus for evaluating an ultraviolet radiation protection effect of this embodiment.

FIG. 1 is a diagram illustrating a schematic configuration of an apparatus for evaluating an ultraviolet radiation protection effect of this embodiment.

Referring to FIG. 1, an ultraviolet radiation protection effect evaluation apparatus 10 is configured to include a light source 11, a filter 12, an optical fiber 13, an irradiation port 14, a skin substitute film 16, a spectrometer 17, a photodetector 18, and a computer 19. This ultraviolet radiation protection effect evaluation apparatus 10 is an apparatus for applying a below-described method of evaluating an ultraviolet radiation protection effect to a measurement sample.

The light source 11, for which a xenon lamp is suitably used in this embodiment, is not limited to this. Further, the light source 11 is connected to the computer 19 described below, so that on-off control of the light source 11 is performed by the computer 19.

The filter 12, which is in the vicinity of the light source 11 in a direction in which light travels from the light source 11, turns a light beam emitted from the light source 11 into a predetermined ultraviolet radiation range such as UVB and UVA ultraviolet radiation of 290 nm to 400 nm wavelengths. This means reproducing a light source in an in vivo SPF measurement site and performing irradiation. The above-described filter 12 generating UVB and UVA ultraviolet radiation of 290 nm to 400 nm wavelengths, for which a WG320 filter and a UG11 filter (both manufactured by SCHOTT AG) are suitably used, is not limited to these, and an appropriate filter is used based on a desired ultraviolet radiation range.

The optical fiber 13 is in the vicinity of the filter 12 in a direction in which light travels from the filter 12. The optical fiber 13 guides ultraviolet radiation that has passed through the filter 12 to the irradiation port 14.

The ultraviolet radiation is emitted from the irradiation port 14. The irradiation port 14 and the photodetector 18 are fixed at a predetermined interval, and the skin substitute film 16, on which a predetermined amount of a sample 15 is applied by a predetermined method, is fixed at a certain distance from the irradiation port 14. The irradiation port 14, the sample 15, the skin substitute film 16, the spectrometer 17, and the photodetector 18 are arranged in this order when indicated in order of light traveling. This arrangement up to the skin substitute film 16 is based on the in vivo SPF measuring method provided by INTERNATIONAL SUN PROTECTION FACTOR (SPF) TEST METHOD, February 2003.

The skin substitute film 16, on which the measurement sample 15 is applied, is a substitute for the skin of a living body in the in vivo SPF measurement, and is preferably composed of a material that does not absorb ultraviolet radiation of 290 nm to 400 nm. Non-Patent Document 1 discloses a method using a medical tape as a skin substitute film. In this embodiment, a PMMA (polymethyl methacrylate) resin plate (Plexiglass™, manufactured by Schonberg GmbH & Co. KG) is suitably used, but the skin substitute film 16 is not limited to this.

The spectrometer 17 spectrally splits light of a 290 nm to 400 nm range at intervals of 1 nm, so that the respective intensities are converted to voltages and further subjected to A/D conversion in the photodetector 18 to be output to the computer 19. In the ultraviolet radiation protection effect evaluation apparatus 10, the photodetector 18 detects a light beam that has passed the above-described measurement sample 15 and skin substitute film 16.

The computer 19, to which the spectral intensities at intervals of 1 nm are input from the photodetector, performs below-described processing to calculate a light exposure time and a final in Vitro predicted SPF in this measurement. Further, as described above, the computer 19 performs on-off control of the light source 11.

The computer 19 is capable of receiving data from the photodetector 18; processing the contents of the data into a format easily understandable by a user; and displaying results on a screen, printing out results on recording paper, or storing results in a storage medium. Further, the computer 19, for which, for example, a general-purpose personal computer can be used, can cause functions in the above-described evaluation apparatus 10 to be executed based on instructions from a user through input means.

[Functional Configuration of Evaluation Apparatus]

Figure 2:
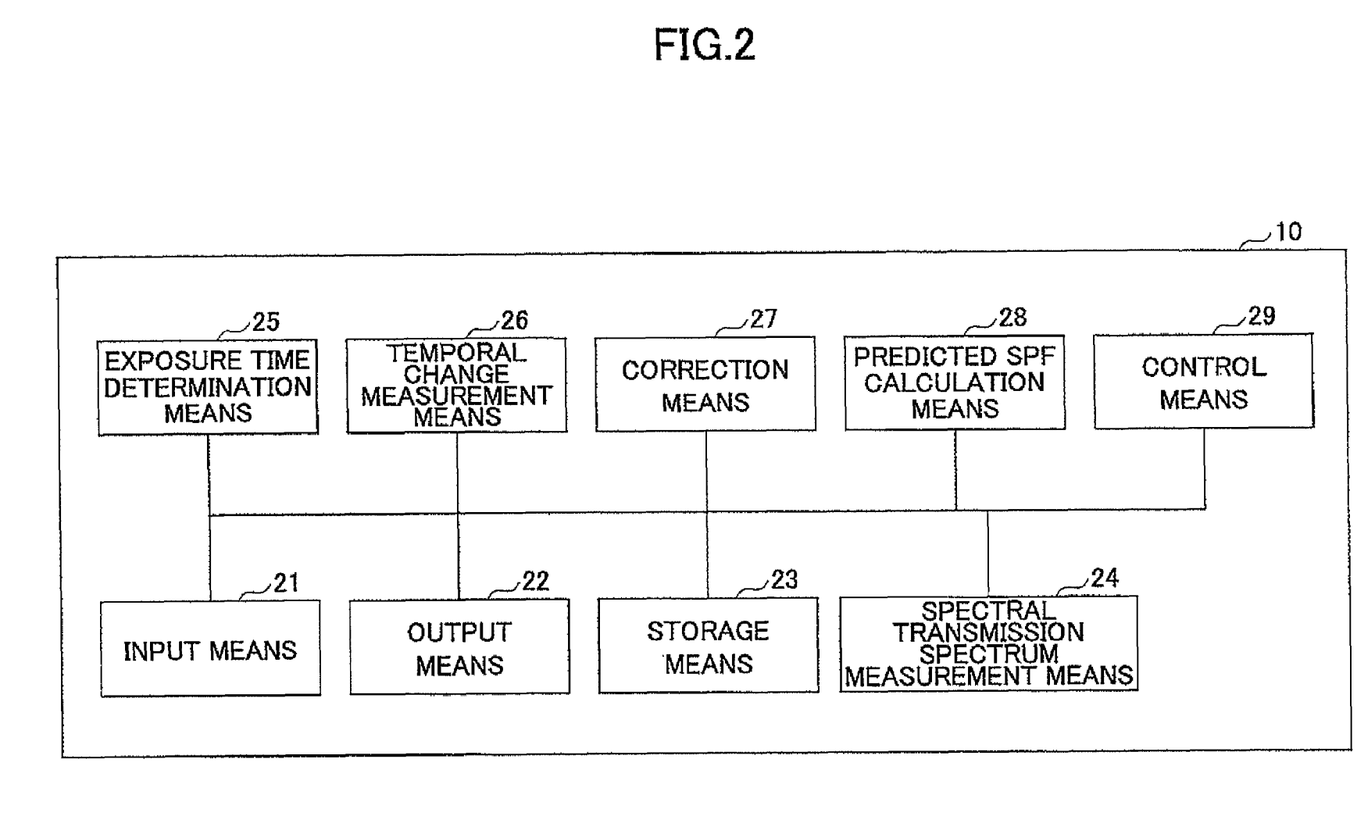
FIG. 2 is a diagram illustrating a functional configuration of the apparatus for evaluating an ultraviolet radiation protection effect of this embodiment.

FIG. 2 is a diagram illustrating a functional configuration of the apparatus for evaluating an ultraviolet radiation protection effect of this embodiment.

Referring to FIG. 2, the ultraviolet radiation protection effect evaluation apparatus 10 is configured to include input means 21, output means 22, storage means 23, spectral transmission spectrum measurement means 24, exposure time determination means 25, temporal change measurement means 26, correction means 27, predicted SPF calculation means 28, and control means 29.

The input means 21, which is provided in, for example, the computer 19, receives various data inputs such as a user's instruction to start evaluation or cause measurement results to be output by the output means 22. The input means 21 is made up of, for example, a keyboard and a pointing device such as a mouse.

The output means 21, which is provided in, for example, the computer 19, displays or outputs the contents of an input through the input means 21 or the contents of what is executed based on the contents of the input. The output means 22 is made up of a display and a loudspeaker. Further, a printer function may be included as the output means 22. In this case, simple measurement results or calculation results can be printed on a printing medium such as paper and provided to a user.

The storage means 23, which is provided in, for example, the computer 19, stores various data such as the results of measurements by the spectral transmission spectrum measurement means 24, the exposure time determined by the exposure time determination means 25, the results of measurements by the temporal change measurement means 26, the correction information obtained by the correction means 27, and the results of calculations by the predicted SPF calculation means 28.

The spectral transmission spectrum measurement means 24, for example, measures the spectral transmission spectrum of the measurement sample 15 at intervals of 1 nm with ultraviolet radiation of 290 nm to 400 nm using the photodetector 18, etc. That is, the spectral transmission spectrum measurement means 24 performs a preliminary measurement for determining a light exposure time in a final measurement. Further, the exposure time determination means 25, as a function of the computer 19, determines a light exposure time based on the spectral transmission spectrum obtained by the preliminary measurement in the spectral transmission spectrum measurement means 24. The details of the preliminary measurement are described below.

The temporal change measurement means 26, as a function of the computer 19, measures a change over time in the spectral transmission spectrum of the measurement sample 15 by light exposure based on the light exposure time determined by the exposure time determination means 25. The temporal change measurement means 26 measures a change over time in the spectral transmission spectrum in the measurement sample 15 due to photodegradation. Thereby, it is possible to calculate in vitro predicted SPFs reflecting the photodegradation phenomenon of a sample due to exposure light.

The correction means 27, as a function of the computer 19, performs correction according to the change over time of the spectral transmission spectrum of the measurement sample 15 based on the measurement results obtained by the temporal change measurement means 26. Further, the predicted SPF calculation means 28 calculates the final in vitro predicted SPF of the measurement sample using the correction result obtained by the correction means.

The control means 29, as a function of the computer 19, controls the entire constituent parts of the evaluation apparatus 10. Specifically, the control means 30 controls, based on, for example, a user's instructions from the input means 21, measuring a spectral transmission spectrum, determining an exposure time, measuring photodegradation, performing correction according to the change over time of the spectral transmission spectrum, and calculating an in vitro predicted SPF. Further, the control means 29, as a function of the computer 19, performs on-off control of the light source 11. The details of the final measurement are described below.

[Preliminary Measurement]

Here, as described below, the photodetector 18 measures a spectral transmission spectrum in an ultraviolet radiation range of, for example, 290 nm to 400 nm at predetermined wavelength intervals in the preliminary measurement. The predetermined wavelength intervals, which may be of, for example, 1 nm or 5 nm, are not limited in particular in the present invention. Accordingly, in the following description, the measurement is performed at intervals of 1 nm by way of example. Further, in order to perform measurement at intervals of 1 nm, the photodetector 18 and the spectrometer 17 are required to have sensitivity characteristic adjusted to this wavelength region, but are not limited in particular. However, the spectrometer 17 is required to have a wavelength resolution of 1 nm or less in order to measure the spectral transmission spectrum at intervals of 1 nm.

In the ultraviolet radiation protection effect evaluation apparatus and method, where the spectral transmission spectrum of a sample is measured, samples with higher SPFs, which are more effective in ultraviolet radiation absorption, resultantly transmit less amounts of light. Therefore, in order to predict the SPF with accuracy even in samples with high SPFs over SPF 50, a photodetector is necessary that has good sensitivity for detecting faint light. Conventionally, photodetectors such as photodiode arrays and CCDs have been commonly used. However, with recent progress in faint light detection techniques, photomultipliers with enhanced detection sensitivity are also often used. It is apparent also theoretically that photomultipliers have higher detection sensitivity than conventional photodiode arrays and CCDs, but it is necessary to select the material of the photoelectric surface of the photomultiplier depending on the wavelength region of light to be detected. In this embodiment, it is possible to even measure samples with high SPFs by using a photomultiplier that have good sensitivity characteristics in a ultraviolet radiation range of 290 nm to 400 nm in particular.

[Preliminary Measurement and Determination of Light Exposure Time]

In this embodiment, a preliminary measurement for measuring the spectral transmission spectrum of a measurement sample is performed prior to a final measurement. A light exposure time in the final measurement is determined from the spectral transmission spectrum of the sample obtained in this preliminary measurement, The method of determining this light exposure time starts first with calculating a provisional in vitro predicted SPF based on the measurement results of reference samples whose in viva SPFs are known.

The analysis method is as follows. The spectral transmission spectra of multiple reference samples having known in vivo SPFs are measured, and a multivariate analysis of the correlations between the spectra and the known in vivo SPFs is conducted from the transmitted light intensity of each wavelength. A provisional in vitro predicted SPF close to the in vivo SPF is determined from a standard curve formed of a group of points plotted based on the relationship between the numerical values determined from this multivariate analysis and the in vivo SPFs.

Further, the multivariate analysis of this embodiment is characterized by using the PLS (Partial Least Squares) regression analysis. The multiple regression analysis, which is usually used, is a method that performs regression analysis using all parameters used in the analysis, and can be used in analyzing data including a large number of factors in principle. However, in the case where the number of explanatory variables is large relative to a response variable, it is not possible to obtain an appropriate regression equation because of excessive fitting. On the other hand, the PLS regression analysis employed in this embodiment is a method of constructing a prediction model in the case where there are a large number of explanatory variables. The PLS regression analysis, whose ultimate goal is a prediction, can be very useful means if there is no practical need to limit the number of factors to be measured. For example, such a case where the data of a spectral spectrum are used as in this case corresponds to this.

Figure 3:
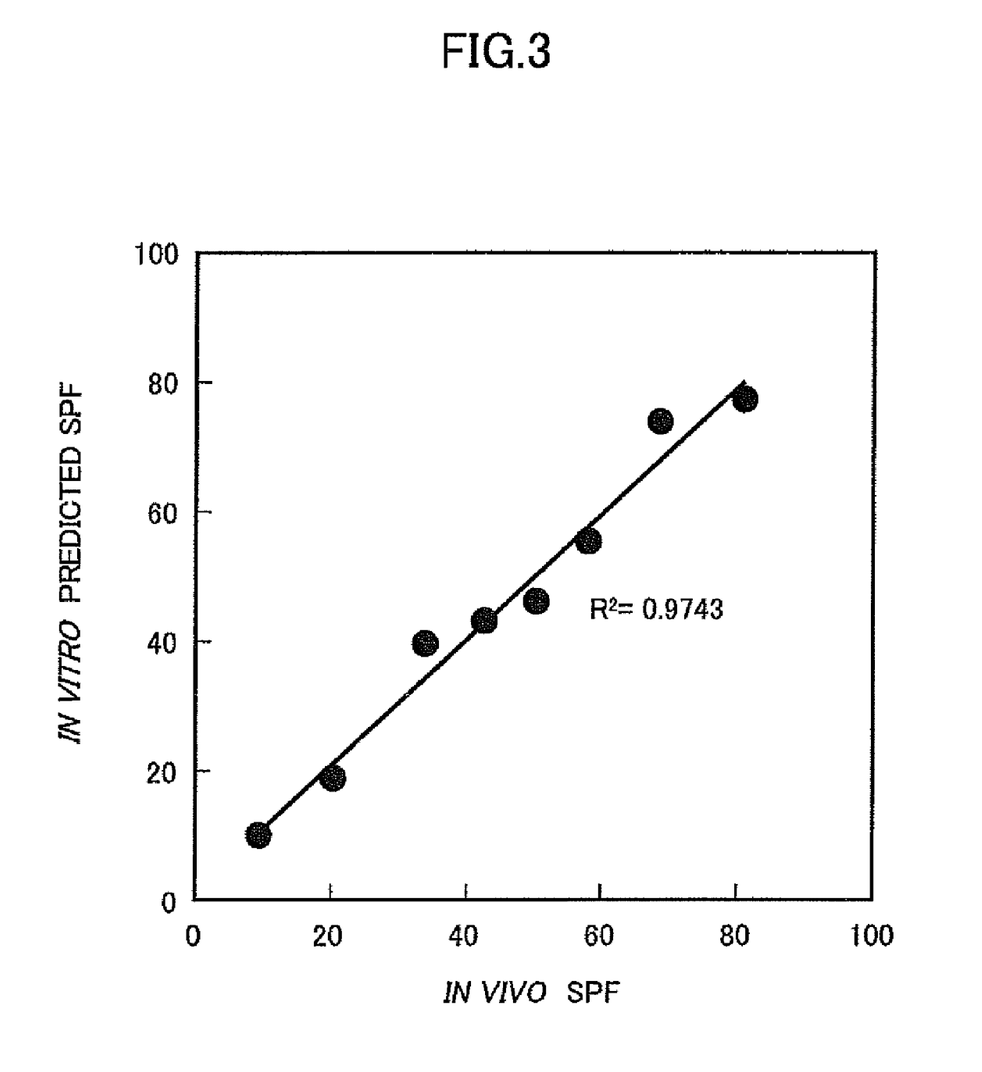
FIG. 3 is a diagram illustrating the correlation between known in vivo SPFs and predicted in vitro SPFs in reference samples of this embodiment.

FIG. 3 is a diagram illustrating the correlation between the in vivo SPF and the in vitro predicted SPF in reference samples.

Referring to FIG. 3, which shows the results of predicting SPFs by the above-described PLS regression analysis in reference samples having known in vivo SPFs, the horizontal axis represents the known in vivo SPFs and the vertical axis represents the in vitro predicted SPFs.

The in vitro predicted SPFs represented by the vertical axis of FIG. 3 are the results of the prediction made in consideration of the photodegradation phenomena of the samples through this preliminary measurement and the below-described final measurement, and the accuracy of the prediction of the in vitro SPFs is high as indicated by a correlation coefficient ($R^2$=0.9743). Accordingly, if the spectral transmission spectrum of a measurement sample is obtained by the preliminary measurement, it is possible to know the SPF of the measurement sample with a certain level of accuracy as a provisional in vitro predicted SPF.

The light exposure time of the measurement sample is determined, under the reproduced conditions of a site of in vivo SPF measurement performed using an actual living body, so as to be proportional to the provisional in vitro predicted SPF so that the light exposure time becomes longer as the in vitro predicted SPF becomes higher. Therefore, the light exposure time is calculated based on 1 MED (Minimal Erythema Dose) in the in vivo SPF measurement site. Here, 1 MED refers to the light amount of ultraviolet radiation necessary to cause a minimal amount of erythema in the tested part of a volunteer in the in vivo SPF measurement site.

With respect to the ultraviolet lamp (solar simulator) used in the in vivo SPF measurement site, the light amount of a light source and the spectrum distribution are standardized. Therefore, 1 MED is expressed mainly in units of time. This is determined in the tested part with application of no sample in the in vivo SPF measurement site.

While there are variation factors such as a human individual difference, a regional difference, an age difference, a gender difference, and a skin type difference as described above, 1 MED is assumed to be in the range of five seconds (0.083 minutes) to 90 seconds (1.5 minutes) in this embodiment. From this assumption, the light exposure time in the final measurement in this embodiment is determined to be more than or equal to the PROVISIONAL IN VITRO PREDICTED SPF×0.08 (minutes) and less than the PROVISIONAL IN VITRO PREDICTED SPF×1.50 (minutes). In terms of data reproducibility, 1 MED is preferably in the range of 10 seconds to 60 seconds and more preferably in the range of 20 seconds to 50 seconds in this embodiment. Calculating the light exposure time based on this conversion results in a light exposure of 50×0.5=25 minutes if the provisional in vitro predicted SPF is 50 in the preliminary measurement and 1 MED is 30 seconds (0.5 minutes).

The light exposure time is calculated in the computer 19. Further, in the below-described final measurement, the computer 19 controls the light source 11 so as to have a predetermined light exposure time.

[Final Measurement and Correction according to Photodegradation]

As the final measurement, the measurement sample is exposed to ultraviolet radiation of 290 nm to 400 nm continuously for the light exposure time calculated from the result of the above-described preliminary measurement. At this point, a change over time in the spectral transmission spectrum of the measurement sample is measured, and correction according to the change of the photodegradation of the measurement sample is performed. Thereafter, a final in vitro predicted SPF is calculated.

Here, the photodegradation phenomenon of a measurement sample refers to a decrease in the original ultraviolet radiation absorbing power due to the isomerization of an organic ultraviolet absorber caused by exposure to light. That is, this means a decrease in the SPF of the measurement sample due to the photodegradation phenomenon. (See, for example, Photodegradation of Sunscreen Chemicals Solvent Consideration, Cosmetics & Toiletries [1999] 105: 41-44.)

This photodegradation phenomenon is considered to be also present in the sample on the skin of a living body because of continuous light exposure in the in vivo SPF measurement site. In this evaluation system, the photodegradation phenomenon can be recognized as a change in the transmission spectrum of the sample with exposure to light, that is, the phenomenon of an increasing amount of light transmission.

The purpose of reproducing the photodegradation phenomenon of the sample is to calculate a highly-accurate final in vitro predicted SPF by measuring a temporal change in the spectral transmission spectrum under the condition of continuous exposure to light and considering a corresponding decrease due to photodegradation in the provisional in vitro predicted SPF obtained in the preliminary measurement, which does not reflect photodegradation.

A change over time in the spectral transmission spectrum of the measurement sample in the final measurement is detected by controlling the light exposure time determined from the above-described preliminary measurement by the second and making it possible to obtain spectral transmission spectrum date at any time intervals during this light exposure time.

Specifically, it is possible to set the condition of the light exposure time by the second, like in minutes and seconds, in the processing by the computer 19. Further, it is also possible, with respect to a change over time in the spectrum during the light exposure time, to obtain the spectrum at any time intervals such as intervals of one minute or time intervals into which the exposure time is equally divided by ten. It is preferable to equally divide a predetermined light exposure time temporally and obtain spectrum data at six or more points (including a light exposure start time of Time zero), more preferably, at 11 or more points. More spectrum data during this period make it possible to get more details of the photodegradation behavior of the sample and thus to increase prediction accuracy.

At this point, in order to accurately understand the photodegradation phenomenon of the measurement sample at the time of its exposure to light, the measurement sample and the entire apparatus are prevented from being moved. To increase prediction accuracy, it is important to obtain a temporal change behavior at the same completely-fixed point.

Correction according to the change of the photodegradation of the measurement sample is performed based on the above-described detection results of the change over time of the spectral transmission spectrum of the measurement sample in this measurement. This correction is achieved by predicting an in vitro SPF from the time-average spectrum of the spectral transmission spectrum of the sample in the ultraviolet radiation range of 290 nm to 400 nm.

As explained in the above-described preliminary measurement, the in vitro predicted SPF can be determined with a certain level of accuracy once the spectral transmission spectrum of the measurement sample is determined. That is, which spectral transmission spectrum is to be adopted to determine the in vitro predicted SPF of the measurement sample based on the understanding of the temporal change behavior of the spectral transmission spectrum due to the photodegradation of the measurement sample in the final measurement is very important in performing measurement with high accuracy.

If the data of the spectral transmission spectrum at Time zero, that is, at the light exposure start time, are adopted, the same value as the provisional in vitro predicted SPF in the preliminary measurement is obtained. However, this numerical value does not reflect the photodegradation phenomenon of the measurement sample due to its continuous exposure to light. Therefore, a numerical value is believed to be predicted that is higher than the SPF that should be predicted. Further, if the data of the spectral transmission spectrum at the latest time just before the end of the light exposure time in the final measurement are adopted, an SPF is believed to be predicted that is lower than what should be the SPF of the measurement sample because the data are spectrum data fully changed by photodegradation, that is, subjected to an excessive light exposure condition.

Therefore, in order to reflect a temporal change, it is supposed to be preferable to predict the in vitro SPF after calculating the total amount of light transmission by the time quadrature of the spectral transmission spectrum as in the phenomenon that skin is exposed with time.

However, in this embodiment, in view of complication of calculations, the calculation method of the time-average spectrum is introduced with respect to the data of the spectral transmission spectrum that change over time. By calculating the in vitro predicted SPF using the idea of this time-average spectrum, it is possible to construct a method of determining a final in vitro predicted SPF that is highly correlated with the in vivo SPF.

The time-average spectrum shown herein is obtained by averaging the spectral transmission intensities of each wavelength of all the data obtained in any number of times, from the spectrum data at the light exposure start time to the last spectrum data of the light exposure time.

Specifically, the final in vitro predicted SPF is calculated from: the standard curve derived by measuring the spectral transmission spectra of the above-described reference samples with known in vivo SPFs and analyzing the correlation between the spectra and the known in vivo SPFs in terms of the transmitted light intensity of each wavelength according to the PLS regression analysis; and the result of correcting the spectral transmission spectrum obtained in this measurement into a time-average spectrum.

By introducing the above-described calculation method, it is possible to predict a final in vitro SPF with respect to samples from those susceptible to photodegradation to those less susceptible to photodegradation using the same calculation method.

[Flow of Method of Evaluating Ultraviolet Radiation Protection Effect]

Figure 4:
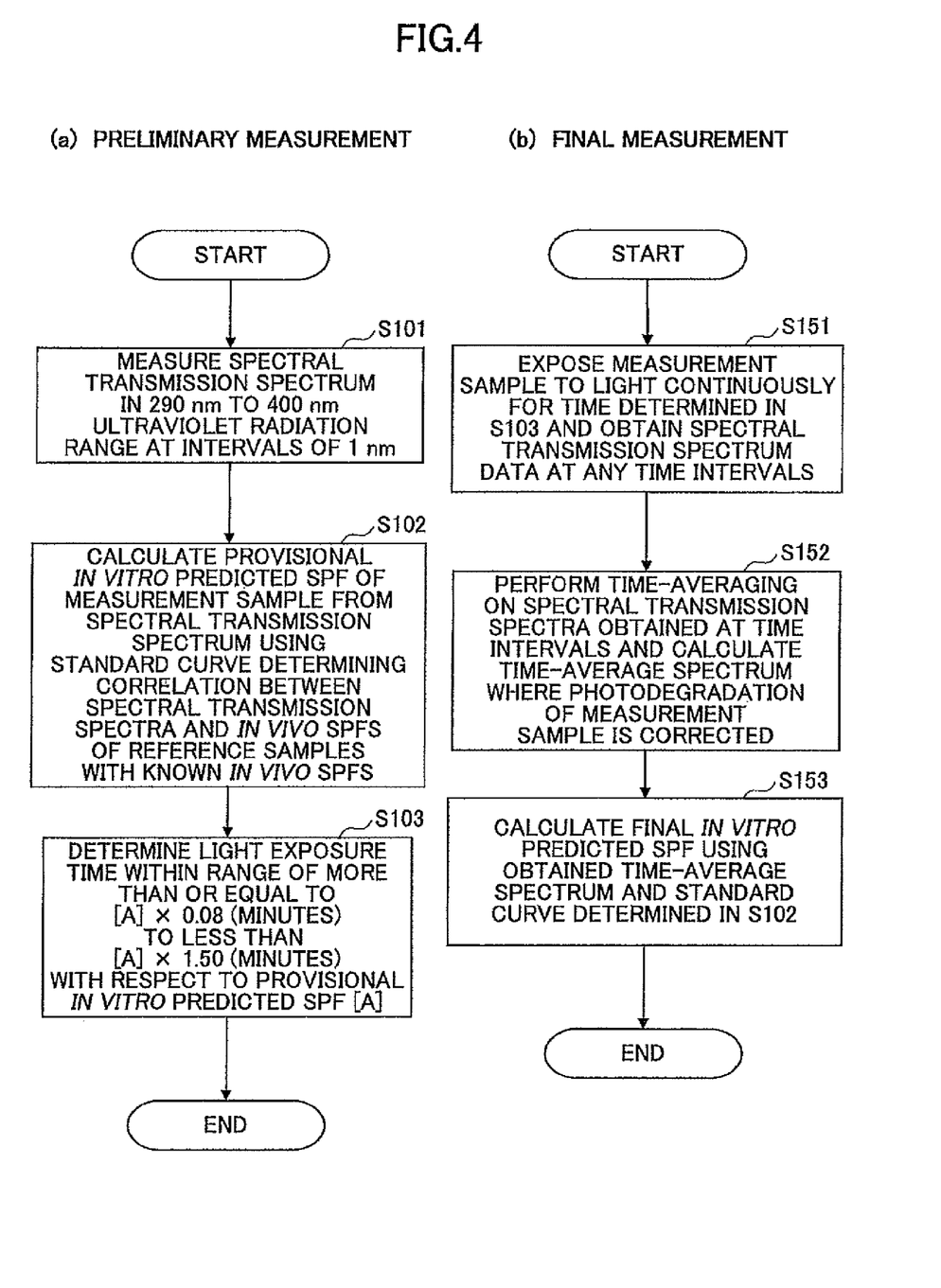
FIG. 4 is a flowchart of a method of evaluating an ultraviolet radiation protection effect of this embodiment.

FIG. 4 is a flowchart of a method of evaluating an ultraviolet radiation protection effect of this embodiment.

The above-described method of evaluating an ultraviolet radiation protection effect is described as a procedure. Referring to FIG. 4(a), which is a flow of the preliminary measurement performed prior to the final measurement, the spectral transmission spectrum of a sample in an ultraviolet radiation range of 290 nm to 400 nm is measured at intervals of 1 nm (S301).

The provisional in vitro predicted SPF of the measurement sample is calculated from the spectral transmission spectrum using a standard curve determining the correlation between the spectral transmission spectra of reference samples with known in vivo SPFs and the in vivo SPFs by a multivariate analysis (S102).

The light exposure time is determined within the range of more than or equal to [A]×0.08 (minutes) to less than [A]×1.50 (minutes) with respect to the provisional in vitro predicted SPF [A] (S103).

Referring to FIG. 4(b), which is a flow of the final measurement performed after the preliminary measurement, the measurement sample is exposed to light continuously for the time determined in S103, and spectral transmission spectrum data are obtained at any time intervals (S151).

Time-averaging is performed on the spectral transmission spectrum obtained at time intervals, and the time-average spectrum of the measurement sample in which its photodegradation is corrected is calculated (S152).

The final in vitro predicted SPF is calculated using the obtained time-average spectrum and the standard curve determined in S102 (S153).

Here, in the above-described embodiment, a description is given of processing where a preliminary measurement is performed prior to a final measurement. However, the preliminary measurement can be omitted as required, for example, if there is the past record of evaluating the same sample in this measurement system, if it is easy to predict, even without measurement records, from similar formulations with measurement records (for example, predicting the SPF of a formulation of 7% titanium oxide as 14 in the case where there are the records of predicting SPF 20 for 10% titanium oxide and SPF 10 for 5% titanium oxide), or if the in vivo SPF is empirically known. That is, the preliminary measurement is important to make a highly-accurate prediction, but may be omitted as required by conditions such as a need to shorten processing time.

under the condition of 25° C. Further, light exposure is performed for 30 seconds per 1 MED in the preliminary measurement.

[Sample Measurement]

Under the above-described measurement conditions, a measurement was performed on Sample A with unknown in vivo SPF. As a result of the preliminary measurement, the provisional in vitro predicted SPF was 29.8. Accordingly, the light exposure time in the final measurement was determined to be 29.8×0.5=14.9 minutes (14 minutes and 54 seconds). In the final measurement, exposure was performed continuously for this light exposure time. Further, the light exposure time of 14 minutes 54 seconds was equally divided into five, so that spectrum data were obtained at six points including the light exposure start time. The time-average spectrum of each wavelength was calculated with respect to these spectrum data at the six points, so that a final in vitro predicted SPF of 21.9 was obtained. This final in vitro predicted SPF was close to the later-obtained in vivo SPF of 22.5. The in vivo SPF and the provisional and final in vitro SPFs of Sample A are shown in Table 1.

TABLE 1

| | MEASUREMENT SAMPLE | PROVISIONAL IN VITRO PREDICTED SPF | FINAL IN VITRO PREDICTED SPF | IN VIVO SPF |
|---|---|---|---|---|
| EXAMPLE 1 | A | 29.8 | 21.9 | 22.5 |
| COMPARATIVE EXAMPLE 1 | | — | 24.6 | |
| COMPARATIVE EXAMPLE 2 | | — | 40.5 | |
| EXAMPLE 2 | B | 70.5 | 62.4 | 64.5 |
| COMPARATIVE EXAMPLE 3 | | — | 33.3 | |
| COMPARATIVE EXAMPLE 4 | | — | 84.6 | |
| EXAMPLE 3 | C | 32.9 | 32.2 | 31.5 |
| COMPARATIVE EXAMPLE 5 | | — | 26.0 | |
| COMPARATIVE EXAMPLE 6 | | — | 81.7 | |

EXAMPLES

A description is given in more detail, with reference to examples, of this embodiment. The following examples illustrate cases where the preliminary measurement is performed.

Example 1

Measurement Conditions

In the measurement apparatus illustrated in the above-described embodiment, a light beam emitted from a xenon lamp light source is caused to pass through a WG320 filter and a UG11 filter (both manufactured by SCHOTT AG), so that a light beam of 290 nm to 400 nm in wavelength is obtained. A PMMA (polymethyl methacrylate) resin plate (Plexlglas™, manufactured by Schonberg GmbH & Co. KG) is used as a skin substitute film, and is placed so as to have an exposure distance of 1 mm to 2 mm from the light source. At this point, the UV-B intensity is caused to be 2.0 MED per minute. The amount of application of a sample onto the PMMA resin plate is 0.75 mg/cm². After weighing a predetermined amount of the sample, the sample was applied on the surface of the PMMA resin plate, being spread with a finger for one minute. After the application, the sample was dried for 15 minutes Example 2

A measurement was performed on Sample B with unknown in vivo SPF under the same measurement conditions as those in Example 1. As a result of the preliminary measurement, the provisional in vitro predicted SPF was 70.5. Accordingly, the light exposure time in the final measurement was determined to be 70.5×0.5=35.25 minutes (35 minutes and 15 seconds). In the final measurement, exposure was performed continuously for this light exposure time. Further, the light exposure time of 35 minutes 15 seconds was equally divided into ten, so that spectrum data were obtained at 11 points including the light exposure start time. The time-average spectrum of each wavelength was calculated with respect to these spectrum data at the 11 points, so that an in vitro predicted SPF of 62.4 was obtained. This in vitro predicted SPF was close to the later-obtained in vivo SPF of 64.5. The in vivo SPF and the provisional and final in vitro SPFs of Sample B are shown in Table 1.

Example 3

A measurement was performed on Sample C with unknown in vivo SPF under the same measurement conditions as those in Example 1. As a result of the preliminary measurement, the provisional in vitro predicted SPF was 32.9. Accordingly, the light exposure time in the final measurement was determined to be 32.9×0.5=16.45 minutes (16 minutes and 27 seconds). In the final measurement, exposure was performed continuously for this light exposure time. Further, the light exposure time of 16 minutes 27 seconds was equally divided into five, so that spectrum data were obtained at six points including the light exposure start time, The time-average spectrum of each wavelength was calculated with respect to these spectrum data at the six points, so that a final in vitro predicted SPF of 32.2 was obtained. This final in vitro predicted SPF was close to the later-obtained in vivo SPF of 31.5. The in vivo SPF and the provisional and final in vitro SPFs of Sample C are shown in Table 1.

It is believed to be because Sample C was hardly affected by photodegradation due to continuous exposure to light that the provisional and final in vitro predicted SPFs were close. This is believed to be because the content of an organic ultraviolet absorber, which is susceptible to photodegradation, was low in the compounding ingredients of Sample C and Sample C was composed mainly of inorganic titanium oxide or zinc oxide.

Comparative Examples 1, 3, and 5

Measurements were performed on Samples A, B, and C described above using the measurement conditions of the second embodiment in Patent Document 1, which is a conventional method, so that their respective in vitro predicted SPFs were obtained. The in vitro predicted SPFs of Samples A, B, and C obtained here are shown in Table 1.

Comparative Examples 2, 4, and 6

Measurements were performed on Samples A, B, and C described above using the conventional method of Non-Patent Document 1, so that their respective in vitro predicted SPFs were obtained. The in vitro predicted SPFs of Samples A, B, and C obtained here are shown in Table 1.

Referring to Table 1, the final in vitro predicted SPEs according to this evaluation method were very close to the later-obtained in vivo SPFs in Examples 1 through 3. It can be said that this result proves the validity of this evaluation method. Further, the final in vitro predicted SPFs according to this evaluation method were closer to the in vivo SPFs than were the in vitro predicted SPFs according to the conventional evaluation methods disclosed in Patent Document 1 and Non-Patent Document 1. Accordingly, it can be said that this evaluation method is superior in prediction of in vivo SPFs to the conventional methods.

According to these examples, it is possible to obtain an in vitro predicted SPF that reflects the photodegradation phenomenon of a sample due to exposure light and shows high correlation with the in vivo SPF even in samples presenting such a high ultraviolet radiation protection effect as SPFs over 50.

Further, the in vitro predicted SPF obtained by this evaluation method is very highly correlated with the in vivo SPF so that it is possible to measure the SPFs of samples with a simple, quick, and highly-accurate method at the stage of developing cosmetic products having a sunburn prevention effect. This makes it possible to reduce the cost of development and to evaluate a large number of samples at the stage of development. Therefore, by using this evaluation method, further acceleration can be expected of the development of cosmetic products that are highly effective in sunburn prevention.

Further, this evaluation method is also applicable to the development or evaluation of nano-materials or ultraviolet absorbers.

A detailed description is given above of a preferred embodiment and examples of the present invention. However, the present invention is not limited to the specific embodiment, and variations and modifications can be made within the scope of the gist of the present invention described in CLAIMS.

The present international application claims priority based on Japanese Patent Application No. 2006-274783, filed on Oct. 6, 2006, the entire contents of which are incorporated in the present international application.

The invention claimed is:

1. A method of evaluating an ultraviolet radiation protection effect, comprising:
   a first step of calculating a correlation from known in vivo SPFs of reference samples and spectral transmission spectra of the reference samples by a multivariate regression analysis, and measuring a change over time in a spectral transmission spectrum of a measurement sample, of which an in vivo SPF is unknown, by an exposure thereof to a light of a light source including an ultraviolet radiation for a preset light exposure time;
   a second step of correcting the change over time in the spectral transmission spectrum of the measurement sample measured by the first step into a time-averaged spectrum; and
   a third step of determining a final in vitro predicted SPF of the measurement sample from the correlation calculated by the first step and the time-average spectrum of the second step.

2. The method of evaluating the ultraviolet radiation protection effect as claimed in claim 1, wherein:
   the first step includes
      a spectral transmission spectrum measurement step of measuring the spectral transmission spectrum of the measurement sample in a predetermined ultraviolet radiation range at predetermined wavelength intervals; and
      an exposure time determination step of determining the light exposure time from the spectral transmission spectrum obtained by the spectral transmission spectrum measurement step.

3. The method of evaluating the ultraviolet radiation protection effect as claimed in claim 2, wherein:
   the exposure time determination step calculates a provisional in vitro predicted SPF of the measurement sample from the correlation and the spectral transmission spectrum of the measurement sample, and determines a time more than or equal to 0.08 times the provisional in vitro predicted SPE and less than 1.50 times the provisional in vitro predicted SPF as the light exposure time.

4. The method of evaluating the ultraviolet radiation protection effect as claimed in claim 2, wherein:
   the spectral transmission spectrum measurement step exposes a skin substitute film having the measurement sample applied thereon to the ultraviolet radiation, the skin substitute film transmitting the ultraviolet radiation, and measures a spectrum of the ultraviolet radiation passing through the measurement sample and the skin substitute film.

5. The method of evaluating the ultraviolet radiation protection effect as claimed in claim 1, wherein:
   the multivariate regression analysis employs a PLS (Partial Least Squares) regression analysis.

6. The method of evaluating the ultraviolet radiation protection effect as claimed in claim 1, wherein:
the first step controls the light exposure time by a one second interval with respect to the change over time in the spectral transmission spectrum of the measurement sample, and obtains data on the spectral transmission spectrum at any time intervals during the light exposure time.

7. The method of evaluating the ultraviolet radiation protection effect as claimed in claim 1, wherein:
the first step measures the change over time in the spectral transmission spectrum due to a photodegradation in the measurement sample.

8. The method of evaluating the ultraviolet radiation protection effect as claimed in claim 1, wherein said first step measures the change over time in the spectral transmission spectrum of the measurement sample at a same completely-fixed point thereof.

* * * * *